United States Patent [19]

True et al.

[11] Patent Number: 4,824,247
[45] Date of Patent: Apr. 25, 1989

[54] METHOD AND APPARATUS FOR MEASURING SPERM PENETRATION

[75] Inventors: Karen J. True, Golden; G. Barbara Griffin, Lakewood; Daniel V. Griffin; William M. Nickels, both of Denver, all of Colo.

[73] Assignee: Avtar Sciences, Inc., Denver, Colo.

[21] Appl. No.: 91,414

[22] Filed: Aug. 31, 1987

[51] Int. Cl.⁴ .................. G01N 21/01; A61B 10/00
[52] U.S. Cl. ............................ 356/244; 350/536
[58] Field of Search .................. 356/244, 246, 36; 350/534, 535, 536

[56] References Cited

U.S. PATENT DOCUMENTS

| | | | |
|---|---|---|---|
| 3,501,242 | 3/1970 | de Mey et al. | 356/246 |
| 3,829,216 | 8/1974 | Persidsky | 356/244 |
| 4,441,793 | 4/1984 | Elkins | 356/244 |
| 4,602,042 | 7/1986 | Chantler et al. | 514/635 |

FOREIGN PATENT DOCUMENTS

| | | | |
|---|---|---|---|
| 120715 | 3/1984 | European Pat. Off. | 356/244 |
| 62126 | 8/1985 | European Pat. Off. | |
| 145702 | 1/1981 | German Democratic Rep. | 350/535 |

Primary Examiner—Richard A. Rosenberger
Attorney, Agent, or Firm—John E. Reilly

[57] ABSTRACT

In a method and apparatus for measuring sperm penetration in vitro through previously collected cervical mucus, a flat, transparent slide has one or more capillary channels which will permit positive introduction of the cervical mucus to one end of each of the channels, and a sperm specimen is placed at the opposite end of each of the channels in direct communication with the cervical mucus in the channels. After incubation, the extent of penetration of the sperm cell specimens through each of the channels can be measured and compared.

15 Claims, 1 Drawing Sheet

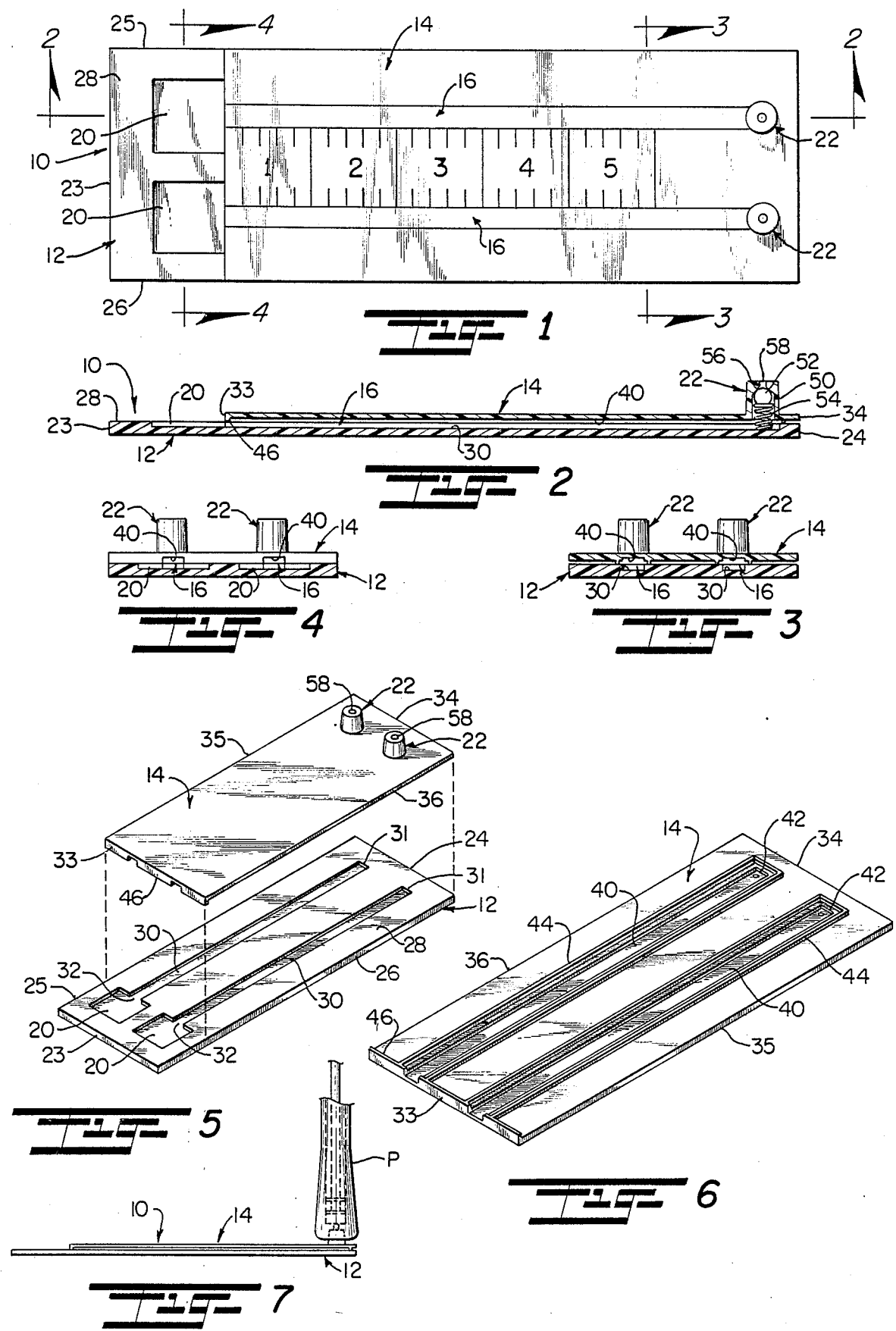

METHOD AND APPARATUS FOR MEASURING SPERM PENETRATION

This invention relates to liquid specimen analysis slides and methods of conducting such analyses; and more particularly relates to a novel and improved method and disposable device for measuring sperm penetration in a laboratory environment.

BACKGROUND AND FIELD OF THE INVENTION

The sperm penetration test, also customarily referred to as the "cervical mucus penetration test", is in widespread use as a means of evaluating the interaction between the sperm and cervical mucus in determining fertility. Sperm penetration is subjectively measured either by testing the female partner's cervical mucus collected after actual intercourse (the post-coital test) or by adding sperm in vitro to previously collected cervical mucus.

As disclosed in a publication of Serono Diagnostics of Braintree, Mass., dated June, 1985, the interaction between sperm and cervical mucus can be tested by placing a pair of flat capillary tubes into a freshly collected sample of semen. After approximately ninety minutes, the penetration into the mucus is measured using a phase contrast or light microscope. In Clin. Exp. Immunol. (1976), 23, 189 there is disclosed a capillary mucus penetration test in which a slide is placed horizontally in a moist or humid chamber with a semen container placed on top of the slide in communication with a capillary tube containing cervical mucus. This test is discussed in *Fertility and Sterility*, Volume 36, No. 3, September, 1981 on page 364 of an article entitled "Penetration of Human Ejaculated Spermatozoa into Human and Bovine Cervical Mucus".

Another type of sperm penetration test, is disclosed in U.S. Pat. No. 4,402,614 to A. Porath-Furedi wherein a slide construction is utilized in combination with an optical magnifier, the slide having a pair of transparent plates separated by plastic beads with the sperm sample deposited in the spaces between the beads so that movement of the sperm can be measured by an optical connector.

There are decided drawbacks in measuring sperm by the methods discussed, particularly those which require handling of the capillary tubes or other measuring devices and increase the possibility of transmission of disease. It is therefore desirable to provide a flat, transparent slide containing one or more capillary channels which will permit the introduction of a medium, such as, cervical mucus into the channel so as to interface with a liquid containing penetrating cells such as semen, to be placed at one end of the channel without user contact of the tested materials yet facilitates accurate measurement of the degree or distance of penetration of the sperm sample through the mucus-filled channel(s).

SUMMARY OF THE INVENTION

It is an object of the present invention to provide for a novel and improved method and apparatus for measuring sperm cell penetration under laboratory conditions which eliminates handling of the apparatus and specimens and greatly minimizes the possibility of transmission of disease.

Another object of the present invention is to provide for a novel and improved analysis slide for measuring sperm cell penetration wherein the slide is disposable, simply constructed and easy to use while avoiding direct contact with the specimen itself.

A further object of the present invention is to provide for a novel and improved method for measuring sperm cell penetration which is efficient and reliable in use and enables accurate comparative reading of two samples at one time.

An additional object of the present invention is to provide for a novel and improved sperm penetration measuring slide of the disposable type in which the cover slip and base plate are united to define one or more capillary channels communicating with a well at one end and so constructed and arranged as to assure proper introduction of a medium to be penetrated, such as, cervical mucus into the channel or channels for measurement of penetrating sperm placed in the well.

In accordance with the present invention, a preferred form of laboratory measurement device comprises a disposable slide having a unitary base plate and cover slip with at least one capillary channel extending between the cover slip and base plate. First means communicates with one portion of the channel for the introduction of a medium to be penetrated, and second means communicates with another portion of said channel designated for the introduction of a specimen which is to be measured, and means are provided for measuring the depth of penetration of the specimen into the medium. Preferably, the first means takes the form of a valve opening with a check valve therein which must be selectively opened by pressure of the fluid introduced so as to assure complete filling of the channel; and the second means preferably takes the form of a well at one end of the channel for deposition of the specimen to be measured or analyzed so as to make contact with the medium to be penetrated.

In the preferred method of measuring sperm cell penetration, the carrier medium is in the form of a cervical mucus which is placed under pressure via one portion of the capillary channel, and the sperm cell specimen is introduced into another portion of the capillary channel with means for calibrating or measuring the extent of penetration of the sperm cell along the channel through the cervical mucus medium.

Other objects, advantages and features of the present invention will become more readily appreciated and understood when taken together with the following detailed description in conjunction with the accompanying drawings, in which:

BRIEF DESCRIPTION OF THE DRAWINGS

FIG. 1 is a top plan view of a preferred form of analysis slide in accordance with the present invention;

FIG. 2 is a cross-sectional view taken about lines 2—2 of FIG. 1;

FIG. 3 is a cross-sectional view taken about lines 3—3 of FIG. 1;

FIG. 4 is a cross-sectional view taken about lines 4—4 of FIG. 1;

FIG. 5 is an exploded view of the major component parts of the preferred form of slide shown in FIGS. 1 to 4;

FIG. 6 is a perspective view of the underside of the cover slip forming a part of the preferred form of invention as shown in FIGS. 1 to 5; and FIG. 7 is a somewhat fragmentary view in elevation illustrating the manner of injection of a liquid into one of the valve openings of the preferred form of the present invention.

DETAILED DESCRIPTION OF THE PREFERRED EMBODIMENT

Referring in detail to the drawings, there is illustrated in FIGS. 1 to 5 a preferred form of analysis slide 10 which is specifically adaptable for use in conducting sperm cell penetration tests. The preferred form of slide 10 is broadly made up of a base plate 12, a cover slip or overlying plate 14, and capillary channels 16 extend in juxtaposed or spaced parallel relation to one another between the base plate 12 and cover slip 14. Each channel 16 terminates at one end of the base plate 12 in a well or shallow entrance area 20 and at the opposite end communicates with a valve port or opening 22 in the cover slip 14.

Considering in more detail the construction and arrangement of elements comprising the slide, it will be seen that the plate 12 is a thin, flat plate composed of a transparent plastic material. The plate 12 is of elongated rectangular configuration which, for the purpose of illustration, is on the order of 28 mm. by 82 mm. The plate has opposite edges 23 and 24 with opposite sides 25 and 26 and a smooth flat upper surface 28 save for channel portions 30 forming the lower portion of the channel 16. The lower channel portions 30 extend intermediately along the greater length of the upper surface 28 and are of shallow rectangular configuration and of a uniform depth throughout. Each channel portion 30 terminates in a first squared end 31 adjacent to the edge 24 and an opposite end 32 which terminates in direct communication with the well 20. Each well 20 is preferably square and of a depth corresponding to that of a communicating channel portion 30 so that the bottom surface of each well 20 is flush with an associated channel portion 30 at the point of entry into the channel portion.

The preferred form of cover slip 14 is of elongated rectangular configuration having a width corresponding to the width of the base plate 12 but being shorter than the base plate. The cover slip 14 is correspondingly composed of a transparent plastic material and preferably is of a lesser thickness than that of the base plate having squared edges 33 and 34 at opposite ends with the edge 34 aligned with the edge 24 of the base plate and the sides 35 and 36 aligned with opposite sides 25 and 26, respectively, of the base plate 12. Furthermore, the edge 33 is aligned with the juncture between the wells 20 and associated channel portions 30 so that the wells 20 are left exposed for the introduction of a specimen in a manner to be described.

The cover slip 14 is further characterized by having a pair of spaced parallel upper channel portions 40 aligned with the lower channel portions 30 when the cover slip 14 is joined in aligned relation to the base plate 12. The upper channel portions 40 correspond in width and depth to that of the lower channel portions 30 and extend for the greater length of the cover plate from the one edge 33 to an opposite squared edge 42 adjacent to the edge 34 of the cover slip, as best seen from FIG. 6. In addition, a downwardly projecting rib or land portion 44 extends around the border of the upper channel portion 40 or, in other words, traverses three sides of the channel portion 40 except at the entrance end 33. A downwardly projecting rib or lip 46 extends across the entrance edge 33 except where it is interrupted by the channel portions 40. When joined together in a manner to be described, the ribs 44 and 46 contact the upper surface 28 of the base plate 12 so as to complete the enclosed capillary channels 16. For example, the total width of each channel 16 is on the order of 3.2 mm. and the depth of each channel 16 is on the order of 0.39 mm. and having a total volume of 79.9 cubic mm.

As illustrated in the drawings, there are a pair of valve ports 22 formed in the cover slip 14, each valve port 22 being aligned with one end of a channel 16 adjacent to the squared edge 42. Each valve opening or port projects upwardly from the cover slip 14 having a larger counterbored portion 50 in which is placed a valve element in the form of a ball 52. The ball 52 is spring-loaded by a coiled spring element 54 to be urged upwardly against an upper rounded seating area 56 which faces downwardly and communicates with a smaller counterbored portion in the form of an orifice 58 extending through the upper wall of the port 22. The lower edge of the port at its interface with the upper channel portion 40 has a stop element 55 for the spring member 54, the spring 54 being inserted into the counterbored portion 50 so as to be mounted or loaded under compression against the ball 52 and to urge the ball upwardly against the seating area 56. It will be evident that a positive downward pressure must be exerted through the orifice 58 and against the upper surface of the ball 52 to force it downwardly against the urging of its spring 54 so as to permit a liquid to be injected through the port 22 into the channel 16.

In carrying out a typical test procedure for sperm penetration, a cervical mucus sample is collected in a tuberculin syringe or pipette. For example, a suitable form of pipette is that sold under the trademark "OVU-TRACK ®" by Recipe Pharma Vertriebs GmbH & Co. KB of Munich, West Germany. A semen sample is collected in a sterile container. The cervical mucus is brought to room temperature with the pipette being placed in a vertical position with the covered end toward the bottom, a conventional form of pipette being represented at P in FIG. 7. By placing in a vertical position, any air bubbles are permitted to travel to the top so as not to interfere with the introduction of the sample. The semen is permitted to liquify for a suitable time period on the order of forty-five minutes or as long as required to permit complete liquefaction. The semen is mixed by swirling the container to insure an even distribution of spermatozoa.

The preferred form of slide 10 is placed on a flat surface with the valve ports 22 in an upright position. A suitable end covering, not shown, is removed from the lower end of the pipette and the pipette P is snugly attached directly to one of the valves. The pipette includes a plunger which is slowly advanced in a downward direction to cause the mucus to be injected into the capillary channel 16 until it surfaces completely and evenly with the opposite open end of the track so as to avoid the formation of a meniscus. The same procedure is then repeated for filling of the second capillary channel with cervical mucus. A large drop of well-mixed semen is deposited in the well or reservoir 20 in direct proximity to the open end of the channel adjacent to the well making sure that the sample interfaces completely with the mucus in such a way that air is not entrapped between the semen and mucus. After a sperm sample has been deposited in each of the wells, the slide is incubated at room temperature for a period of approximately ninety minutes. Thereafter, the slide is placed under a phase optics microscope and, starting at the entrance end of each channel, is focused on the spermatozoa. With a 40× objective, each channel is viewed by advancing the slide in a direction such that the microscope traverses the length of the channel toward the valve 22. Generally the distance traveled by the sperm is the furthest point away from the entrance where ten sperm per HPF is observed. The same procedure is then repeated for the second channel in determining the migration distance of the sperm in that channel. Both distances are measured employing the calibrated measurements as indicated at M across the upper surface of the slide. If the resultant distance measured in each channel agrees within some specified tolerance, such as, 15 mm. the test may be regarded as completed and reliable results attained. If the migration distances do not agree within the specified tolerance, the test can then be repeated on another slide. It should be noted in testing whether any vibration or quaking of the spermatozoa was observed.

For the purpose of illustration, penetration is regarded as normal if in the range of 30 mm. or more. Abnormal is in the range of less than 20 mm. or more and borderline if in the range of 20 mm. to 30 mm. Normal results with a normal volume of 1.5 ml. to 5.0 ml. indicates a probable normal sperm concentration, adequate motility, and the lack of head or neck antibodies. If tests results are borderline, the test should be repeated. If bovine cervical mucus is used rather than human mucus, sperm antibodies may no longer be considered. Bovine mucus collected during estrus may be used, care being taken to collect same under sanitary conditions while avoiding contamination with urine, feces or blood. The clear, viscous mucus should be directly evaluated for adequate spinnbarkeit and ferning before storage in tuberculin syringes at −20° C. for up to six months. Each pool of mucus should be checked with normal sperm prior to testing.

Sperm penetration testing has been carried out employing slides constructed in accordance with the present invention having an overall length of 82.0 mm., a width of 28.0 mm. and depth of 1.3 mm. The length of each capillary channel is 64.0 mm. with a width of 3.2 mm. and a depth of 0.39 mm. The total volume of each channel was 79.9 cubic mm. The well 20 at the end of each channel was of a length of 9.0 mm., a width of 7.0 mm. and a depth of 0.39 mm. with a total volume of 24.9 cubic mm. The valve 22 contained an orifice 58 which is 1.2 mm. in diameter, a ball 1.6 mm. in diameter and a stainless steel spring 54 having a spring rate of 0.665 N/mm.

In the preferred form, the slide 10 is disposable and should be discarded after a test has been conducted whether or not the test is successful. The flat unitary construction of the slide and associated valve ports 22 makes it possible to carry out testing without human contact with the specimens and greatly reduces the number of steps required in carrying out each test procedure. In particular, the valve members enable positive introduction of the mucus into each channel so as to completely fill the channel and avoid the introduction of entrapped air as described. This has been found to assure much greater accuracy and ease in filling and testing and, as the pipette is removed from the valve, the valve will return to a closed position so as to prevent accidental removal or withdrawal of the mucus. Although the preferred form of slide 10 has been described as being composed of a plastic material, it will be evident that other materials may be employed if desired. Further, in the construction of the valve and seating area, suitable modifications may be made in the precise construction of the valves, their ports or openings and associated seating areas in carrying out the objectives of the present invention.

It is therefore to be understood that various modifications and changes may be made in the construction and arrangement of the preferred form of slide as well as the exact sequence of steps in carrying out a test procedure without departing from the spirit and scope of the present invention as defined by the appended claims.

We claim:

1. Apparatus for measuring sperm penetration comprising:
    an elongated slide having a unitary base plate and a cover slip overlying said base plate, and an elongated channel extending longitudinally between said base plate and said cover slip;
    first means communicating with one end portion of said channel for introduction of a liquid medium, including means for releasably closing said one end portion of said channel; and
    second means communicating with an opposite end portion of said channel spaced from said one end portion for the introduction of a specimen to be measured, at least that portion of said cover slip overlying said channel being transparent for viewing of the extent of penetration of the specimen into said medium.

2. Apparatus according to claim 1, said first means including an orifice extending through said cover slip into communication with said channel.

3. Apparatus according to claim 1, wherein said second means includes a well in said base plate at said opposite end portion of said channel.

4. Apparatus according to claim 1, said cover slip being shorter than said base plate, and a well disposed beyond said cover slip into which the sperm specimen is deposited.

5. Apparatus according to claim 1, wherein said cover slip has a thickness compatible for use with optical microscope viewing.

6. Apparatus according to claim 1, there being a pair of said channels in juxtaposed relation to one another, and said second means defined by a pair of wells at said opposite end portion of said base plate, each said well communicating with one of said channels.

7. Apparatus according to claim 1, said first means including a check valve at said one end portion of said channel for the introduction of a cervical mucus as a medium into said channel.

8. Apparatus according to claim 7, there being a pair of said channels in juxtaposed relation to one another, said first means defined by a check valve at one end portion of each said channel, and said second means defined by a pair of wells, there being one of said wells disposed at said opposite end portion of each said channel to that of each said check valve.

9. Apparatus according to claim 8, said channels each having channel portions formed in confronting surfaces of said cover slip and said base plate, respectively.

10. Apparatus for measuring sperm penetration comprising:
    a disposable elongate transparent slide having a unitary base plate and a cover slip overlying said base plate, and at least one elongated capillary channel extending longitudinally between said base plate and said cover slip;

first means communicating with one portion of said channel for introduction of a sperm penetrating medium, said first means including an orifice extending through said cover slip into communication with said channel and a check valve in said orifice; and second means Communicating with another portion of said channel spaced from the one portion for the introduction of a sperm specimen to be measured, said second means including a well at one end of said channel with said first means disposed at an opposite end of said channel.

11. Apparatus according to claim 10, said cover slip being shorter than said base plate, and said well disposed at one end of said base plate beyond said cover slip, said cover slip having a thickness compatible for use with optical microscope viewing.

12. Apparatus according to claim 10, there being a pair of capillary channels in juxtaposed relation to one another, said capillary channels each having channel portions formed in confronting surfaces of said cover slip and said base plate, respectively.

13. A method of measuring penetration of a sperm cell specimen into a cervical mucus comprising the steps of:

injecting cervical mucus under pressure through a normally closed port at one end of a horizontally extending capillary channel and filling said channel until the cervical mucus reaches the opposite end of said channel;

depositing the sperm cell specimen to be measured at the opposite end of said channel into direct communication with the cervical mucus;

incubating the specimen for a predetermined period of time necessary to enable further penetration of the sperma, cells through the cervical mucus; and measuring the extent of penetration of the sperm cells after incubation by optical viewing.

14. The method according to claim 13 wherein said sperm cell specimen is deposited in a recessed area at the opposite end of said channels.

15. The method according to claim 13, including the further step of providing a pair of horizontally extending, juxtaposed capillary channels, injecting cervical mucus into each of said channels, depositing the sperm cell specimens at the opposite end of each channel, and comparing the extent of penetration of each sperm cell specimen through the cervical mucus in each channel.

* * * * *

UNITED STATES PATENT AND TRADEMARK OFFICE
CERTIFICATE OF CORRECTION

PATENT NO. :  4,824,247
DATED      :  25 April, 1989
INVENTOR(S) :  True, Karen J. et al It is certified that error appears in the above—identified patent and that said Letters Patent is hereby corrected as shown below:

Column 6 (Claim 10), Line 66    Cancel "elongate" and substitute -- elongated --

Column 6 (Claim 10), Line 68    After "one", insert -- narrow --

Column 7 (Claim 10), Line 10    Cancel "Communicating" and substitute -- communicating --

Column 8 (Claim 13), Line 14    Cancel "sperma" and substitute -- sperm --

Signed and Sealed this
Fourteenth Day of November, 1989

*Attest:*

JEFFREY M. SAMUELS

*Attesting Officer*   *Acting Commissioner of Patents and Trademarks*